(12) United States Patent
Lin et al.

(10) Patent No.: US 8,222,363 B2
(45) Date of Patent: Jul. 17, 2012

(54) SILICONE ORGANIC ELASTOMER GELS FROM ORGANOPOLYSILOXANE RESINS

(75) Inventors: Shaow Burn Lin, Midland, MI (US); Lori Ann Stark-Kasley, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 315 days.

(21) Appl. No.: 12/680,212

(22) PCT Filed: Sep. 22, 2008

(86) PCT No.: PCT/US2008/077167
§ 371 (c)(1),
(2), (4) Date: Mar. 26, 2010

(87) PCT Pub. No.: WO2009/042535
PCT Pub. Date: Apr. 2, 2009

(65) Prior Publication Data
US 2010/0247460 A1    Sep. 30, 2010

Related U.S. Application Data

(60) Provisional application No. 60/975,365, filed on Sep. 26, 2007.

(51) Int. Cl.
*A61K 8/58* (2006.01)
(52) U.S. Cl. ............ 528/15; 528/31; 524/268; 524/588; 424/401; 424/70.121
(58) Field of Classification Search ............... 528/15, 528/31; 424/401, 70.121; 524/588, 268; 556/445
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,296,291 A | 1/1967 | Chalk | |
| 3,419,593 A | 12/1968 | Willing | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 4,122,029 A | 10/1978 | Gee et al. | |
| 4,987,169 A | 1/1991 | Kuwata et al. | |
| 5,036,117 A | 7/1991 | Chung et al. | |
| 5,175,325 A | 12/1992 | Brown et al. | |
| 5,236,986 A | 8/1993 | Sakuta | |
| 5,380,527 A | 1/1995 | Legrow et al. | |
| 5,387,417 A | 2/1995 | Rentsch | |
| 5,412,004 A | 5/1995 | Tachibana et al. | |
| 5,488,124 A * | 1/1996 | Cobb et al. ................... | 556/445 |
| 5,493,041 A | 2/1996 | Biggs et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,869,727 A | 2/1999 | Crane et al. | |
| 5,880,210 A | 3/1999 | Schulz, Jr. et al. | |
| 5,889,108 A | 3/1999 | Zhang | |
| 5,919,441 A | 7/1999 | Mendolia et al. | |
| 5,929,162 A | 7/1999 | Horne et al. | |
| 5,929,164 A | 7/1999 | Zhang | |
| 5,981,680 A | 11/1999 | Petroff et al. | |
| 5,998,542 A | 12/1999 | Horne et al. | |
| 6,013,682 A | 1/2000 | Dalle et al. | |
| 6,051,216 A | 4/2000 | Barr et al. | |
| 6,200,581 B1 | 3/2001 | Lin et al. | |
| 6,207,717 B1 | 3/2001 | Lin et al. | |
| 6,262,170 B1 | 7/2001 | Kilgour et al. | |
| 6,271,295 B1 | 8/2001 | Powell et al. | |
| 6,291,563 B1 | 9/2001 | Horne et al. | |
| 6,331,604 B1 | 12/2001 | Wang et al. | |
| 6,365,670 B1 | 4/2002 | Fry | |
| 6,531,540 B1 | 3/2003 | O'Brien | |
| 6,605,734 B2 | 8/2003 | Roy et al. | |
| 7,078,026 B2 | 7/2006 | Ferrari et al. | |
| 7,241,835 B2 * | 7/2007 | O'Brien et al. ............... | 524/862 |
| 2001/0041771 A1 | 11/2001 | Kondo et al. | |
| 2003/0072730 A1 | 4/2003 | Tournilhac | |
| 2003/0170188 A1 | 9/2003 | Ferrari et al. | |
| 2003/0235553 A1 | 12/2003 | Lu et al. | |
| 2004/0091440 A1 | 5/2004 | Kamei et al. | |
| 2004/0092655 A1 | 5/2004 | Otomo | |
| 2004/0180032 A1 | 9/2004 | Manelski et al. | |
| 2004/0228821 A1 | 11/2004 | Sunkel et al. | |
| 2009/0317343 A1 | 12/2009 | Lin et al. | |
| 2010/0158824 A1 * | 6/2010 | Lin ........................... | 424/59 |
| 2010/0172849 A1 | 7/2010 | Shaow et al. | |
| 2010/0183525 A1 | 7/2010 | Lin | |

FOREIGN PATENT DOCUMENTS

| | | |
|---|---|---|
| EP | 0922734 | 6/1999 |
| EP | 1148099 | 10/2001 |
| EP | 1266648 | 12/2002 |
| EP | 1266653 | 12/2002 |
| EP | 1057872 | 2/2006 |
| EP | 1266647 | 5/2007 |
| JP | 06-049347 | 2/1994 |
| JP | 2001-213963 | * 8/2001 |
| WO | 9913859 | 3/1999 |
| WO | WO99/13859 | 3/1999 |
| WO | 0114458 | 3/2001 |
| WO | WO01/14458 | 3/2001 |
| WO | 03093349 | 11/2003 |
| WO | 03093369 | 11/2003 |
| WO | WO03/093349 | 11/2003 |
| WO | WO03/093369 | 11/2003 |

(Continued)

OTHER PUBLICATIONS

English language abstract, machine generated English translation 2001-213963, Aug. 2001.*

(Continued)

*Primary Examiner* — Margaret Moore
(74) *Attorney, Agent, or Firm* — Alan Zombeck

(57) ABSTRACT

Gel compositions are disclosed comprising a silicone elastomer from the reaction of an SiH containing organopolysiloxane resin and an organic compound having at least two aliphatic unsaturated groups in its molecule.

5 Claims, No Drawings

| | FOREIGN PATENT DOCUMENTS | |
|---|---|---|
| WO | 03101412 | 12/2003 |
| WO | WO03/101412 | 12/2003 |
| WO | WO03/105789 | 12/2003 |
| WO | WO03/105801 | 12/2003 |
| WO | WO03/106614 | 12/2003 |
| WO | WO2004/000247 | 12/2003 |
| WO | WO2004/054523 | 7/2004 |
| WO | WO2004/054524 | 7/2004 |
| WO | WO2004/060101 | 7/2004 |
| WO | WO2004/060271 | 7/2004 |
| WO | WO2004/060276 | 7/2004 |
| WO | 2004084844 | 10/2004 |
| WO | WO2004/103323 | 12/2004 |
| WO | WO2005/100444 | 10/2005 |
| WO | WO2007/109240 | 9/2007 |
| WO | WO2007/109260 | 9/2007 |
| WO | WO2007109282 | 9/2007 |
| WO | WO2008/085360 | 7/2008 |
| WO | WO2009/042535 | 4/2009 |

OTHER PUBLICATIONS

"Synthesis of New Organic Crosslinking Reagents Containing SiH Bonds and Curing System Thereof" authored by Iwahara et al. and published in Polymer Journal (1993) 25 (4), 379-389.

* cited by examiner

SILICONE ORGANIC ELASTOMER GELS FROM ORGANOPOLYSILOXANE RESINS

CROSS REFERENCE TO RELATED APPLICATIONS

This application is a U.S. national stage filing under 35 U.S.C. §371 of PCT Application No. PCT/US08/77167 filed on Sep. 22, 2008, currently pending, which claims the benefit of U.S. Provisional Patent Application No. 60/975365 filed Sep.26, 2007 under 35 U.S.C. §119 (e). PCT Application No. PCT/US08/77167 and U.S. Provisional Patent Application No. 60/975365 are hereby incorporated by reference.

TECHNICAL FIELD

This disclosure relates to gel compositions comprising a silicone elastomer from the reaction of an SiH containing organopolysiloxane resin and an organic compound having at least two aliphatic unsaturated groups in its molecule.

BACKGROUND

Silicone elastomer gels have been used extensively to enhance the aesthetics of personal care formulations by providing a unique sensory profile upon application. Most silicone elastomer gels are obtained by a crosslinking hydrosilylation reaction of an SiH polysiloxane with another polysiloxane containing an unsaturated hydrocarbon substituent, such as a vinyl functional polysiloxane, or by crosslinking an SiH polysiloxane with a hydrocarbon diene. The silicone elastomers may be formed in the presence of a carrier fluid, such as a volatile silicone, resulting in a gelled composition. Alternatively, the silicone elastomer may be formed at higher solids content, subsequently sheared and admixed with a carrier fluid to also create gels or paste like compositions. Representative examples of such silicone elastomers are taught in U.S. Pat. Nos. 5,880,210, and 5,760,116.

While silicone elastomers have provided significant advances for improving personal care formulation, they possess several shortcomings that have limited their use. For example, silicone elastomers having mostly dimethyl siloxane content are less effective for gelling organic based solvents and carrier fluids. Silicone elastomer gel compositions having high dimethyl siloxane also have limited compatibility with many personal care ingredients. For example, the widely used sunscreen agent, octyl methoxycinnamate, has limited solubility in many of these silicone elastomer gels. Another problem is the reduction of viscosity of the silicone elastomer gel in the presence of such incompatible components. Thus, there is a need to identify silicone elastomers that can gel organic solvents. Furthermore, there is a need to identify silicone elastomer gels having improved compatibilities with many personal care ingredients, while maintaining the aesthetics associated with silicone organic elastomer gels. To this end, there have been many attempts to improve compatibilities of silicone elastomers with various personal care ingredients wherein alkyls, polyether, amines or other organofunctional groups have been grafted onto the silicone organic elastomer backbone. Representative of such organofunctional silicone elastomers are taught in U.S. Pat. Nos. 5,811,487 , 5,880,210 , 6,200,581, 5,236,986, 6,331,604 , 6,262,170 , 6,531,540, and 6,365,670.

However, there is still a need to improve the compatibility of silicone elastomer based gels, and in particular, with organic based volatile fluids and personal care ingredients. Such improved compatibility should not sacrifice sensory aesthetic profiles. Furthermore, the gelling or thickening efficiency of the silicone elastomer in a carrier fluid should be maintained or improved.

The present inventors have discovered silicone organic elastomers based on certain organopolysiloxane resins that provide gelled compositions of carrier fluids efficiently. The resulting gelled compositions also possess additional benefits, such as improved compatibilities with many common personal care ingredients, while maintaining sensory aesthetics.

SUMMARY

This disclosure relates to a gel composition comprising a silicone elastomer from the reaction of:
A) an SiH containing organopolysiloxane resin.
B) an organic compound having at least two aliphatic unsaturated groups and in its molecule, and
C) a hydrosilylation catalyst,
and;
D) an optional carrier fluid,
E) an optional personal or healthcare active,
wherein the gel composition has a hardness of at least 0.03 Newton force.

DETAILED DESCRIPTION

A) The SiH Containing Organopolysiloxane Resin

Component (A) in the present invention is an organopolysiloxane resin having at least one SiH unit in its molecule. Organopolysiloxanes contain any number of $(R_3SiO_{1/2})$, $(R_2SiO_{2/2})$, $(RSiO_{3/2})$, or $(SiO_{4/2})$ siloxy units. The formula for an organopolysiloxane may be designated by the average of the siloxy units in the organopolysiloxane as follows; $R_nSiO_{(4-n)/2}$, where the R is independently any organic group, alternatively a hydrocarbon, or alternatively an alkyl group, or alternatively methyl. The value of n in the average formula may be used to characterize the organopolysiloxane. For example, an average value of n=1 would indicate a predominate concentration of the $(RSiO_{3/2})$ siloxy unit in the organopolysiloxane, while n=2 would indicate a predominance of $(R_2SiO_{2/2})$ siloxy units. As used herein, "organopolysiloxane resin" refers to those organopolysiloxanes having a value of n less than 1.8 in the average formula $R_nSiO_{(4-n)/2}$, indicating a resin. When R is methyl in the siloxy unit formulas of an organopolysiloxane, the respective siloxy units are often designated as M, D, T or Q siloxy units. The organopolysiloxane useful as component A) in the present disclosure contain at least one SiH siloxy unit, that is, there is at least one $(R_2HSiO_{0.5})$, (RHSiO), or a $(HSiO_{1.5})$ siloxy unit present in the molecule. These siloxy units can be represented as $M^H$, $D^H$, and $T^H$ siloxy units respectively when R is methyl. The SiH containing organopolysiloxane may be selected from any SiH containing organopolysiloxane resins considered to be a silsesquioxane resin or a "MQ" resin.

In one embodiment, the SiH containing organopolysiloxane resin comprises the formula;

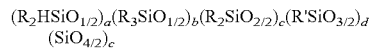
$(R_2HSiO_{1/2})_a(R_3SiO_{1/2})_b(R_2SiO_{2/2})_c(R'SiO_{3/2})_d(SiO_{4/2})_e$ where a is greater than 0
b is from 0 to 0.8
c is from 0 to 0.4
d is from 0 to 0.95
e is from 0 to 0.9, alternatively 0 to 0.95
with the provisos that at least d or e is greater than zero, and sum of a, b, c, d, and e is at least 0.9, R is an organic group as defined above, typically R is methyl.

R' is a monovalent hydrocarbon group having 2 to 8 carbon atoms.

R' can be a linear or branched alkyl such as ethyl, propyl, butyl, pentyl, hexyl, heptyl, or octyl group. R' can also be an aryl or alkylaryl such as phenyl, alkylphenyl group. Typically, R' is propyl.

In the $(R_2HSiO_{1/2})_a(R_3SiO_{1/2})_b(R_2SiO_{2/2})_c(R'SiO_{3/2})_d(SiO_{4/2})_e$ formula above, and subsequent use below, the subscripts a, b, c, d, and e represents the mole fraction of each siloxy unit designated. The sum of a, b, c, d, and e is at least 0.9, and d and e is greater than 0. Thus, the SiH containing organohydrogensiloxane resin may contain additional siloxy units, such as silanol and or alkoxy functional siloxy units.

In a further embodiment, the SiH containing organopolysiloxane resin is an SiH containing silsesquioxane resin comprising the formula $(Me_2HSiO_{1/2})_a(Me_2SiO_{2/2})_c(R'SiO_{3/2})_d$ where a is greater than 0
  c is from 0 to 0.4
  d is from 0 to 0.9
  with the proviso that sum of a, c, d, and e is at least 0.9, and d is greater than zero
R' is a monovalent hydrocarbon group having 2 to 8 carbon atoms, as discussed above, and Me is methyl.

In yet a further embodiment, the SiH containing organopolysiloxane resin is an SiH containing MQ resin comprising the formula $(Me_2HSiO_{1/2})_a(Me_3SiO_{1/2})_b(SiO_{4/2})_e$ where
  a is greater than 0
  b is from 0 to 0.8
  e is from 0 to 0.9, alternatively 0 to 0.95
    with the proviso that the sum of a, b, and e is at least 0.9, and e is greater than 0,
  Me is methyl.

Methods for preparing the SiH containing organopolysiloxane resin useful as component A are known, such as those described in WO 2005/100444, which is hereby incorporated by reference.

(B) The Organic Compound Having at Least Two Aliphatic Unsaturated Hydrocarbon Groups in its Molecule Component (B) is an organic compound, or any mixture of compounds, containing at least two aliphatic unsaturated groups in its molecule. The compound may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturation groups are at the termini of the compound, or pendant if part of a polymeric compound. Compounds containing terminal or pendant unsaturated groups can be represented by the formula $R^2—Y—R^2$ where $R^2$ is a monovalent unsaturated aliphatic hydrocarbon group containing 2 to 12 carbon atoms, and Y is a divalent organic or siloxane group or a combination of these. Typically $R^2$ is $CH_2=CH—$, $CH_2=CHCH_2—$, $CH_2=C(CH_3)CH_2—$ or $CH\equiv C—$, and similar substituted unsaturated groups such as $H_2C=C(CH_3)—$, and $HC\equiv C(CH_3)—$.

The compound having the formula $R^2—Y—R^2$ as component B) may be considered as being a "organic", "hydrocarbon", "organic polymer", "polyether" or "siloxane", or combinations thereof, depending on the selection of Y. Y may be a divalent hydrocarbon, a siloxane, polyoxyalkylene, polyalkylene, a polyisoalkylene, a hydrocarbon-silicone copolymer, or mixtures thereof.

In one embodiment, the component (B) is selected from an organic compound, herein denoted as $(B_1)$ having the forum a $R^2—Y^1—R^2$ where $R^2$ is a monovalent unsaturated aliphatic group containing 2 to 12 carbon atoms and $Y^1$ is a divalent hydrocarbon. The divalent hydrocarbon $Y^1$ may contain 1 to 30 carbons, either as aliphatic or aromatic structures, and may be branched or un-branched. Alternatively, the linking group $Y^1$ in $B^1$ may be an alkylene group containing 1 to 12 carbons. Component $(B^1)$ may be selected from α,ω-unsaturated alkenes or alkynes containing 1 to 30 carbons, and mixtures thereof. Component $(B^1)$ may be exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

In another embodiment, the component (B) is selected from a $R^2—Y^2—R^2$ compound where $Y^2$ is a siloxane, herein denoted as $(B^2)$. The $Y^2$ siloxane group may be selected from any organopolysiloxane bonded to at least two organic groups having aliphatic unsaturation, designated as $R^2$, to form $R^2—Y^2—R^2$ structures. Thus, component $(B^2)$ can be any organopolysiloxane, and mixtures thereof, comprising at least two siloxane units represented by the average formula $R^2R_mSiO_{(4-m)/2}$
wherein
  R is an organic group,
  $R^2$ is a monovalent unsaturated aliphatic group as defined above, and
  m is zero to 3

The $R^2$ group may be present on any mono, di, or tri siloxy unit in an organopolysiloxane molecule, for example; $(R^2R_2SiO_{0.5})$, $(R^2RSiO)$, or $(R^2SiO_{1.5})$; as well as in combination with other siloxy units not containing an $R^2$ substituent, such as $(R_3SiO_{0.5})$, $(R_2SiO)$, $(RSiO_{1.5})$, or $(SiO_2)$ siloxy units where R is independently any organic group, alternatively a hydrocarbon containing 1 to 30 carbons, alternatively an alkyl group containing 1 to 30 carbons, or alternatively methyl; providing there are at least two $R^2$ substituents in the organopolysiloxane.

Representative, non-limiting, examples of such siloxane based $R^2—Y^2—R^2$ structures suitable as component $(B^2)$ include;

$(R_2R^2SiO_{0.5})(SiO_2)_w(R_2R^2SiO_{0.5})$ $(R_2R^2SiO_{0.5})(SiO_2)_w(R_2SiO)_x(R_2R^2SiO_{0.5})$ $(R_2R^2SiO_{0.5})(R_2SiO)_x(R_2R^2SiO_{0.5})$ $(R_3SiO_{0.5})(R_2SiO)_x(R^2RSiO)_y(R_3SiO_{0.5})$ $(R_3SiO_{0.5})(R_2SiO)_x(R^2RSiO)_y(RSiO_{1.5})_z(R_3SiO_{0.5})$ $(R_3SiO_{0.5})(R_2SiO)_x(R^2RSiO)_y(SiO_2)_w(R_3SiO_{0.5})$ where $w\geq 0$, $x\geq 0$, $y\geq 2$, and z is $\geq 0$. R is an organic group, and
$R^2$ is a monovalent unsaturated aliphatic hydrocarbon group.

$B^2$ may be selected from vinyl functional polydimethylsiloxanes (vinyl siloxanes), such as those having the average formula;

$CH_2=CH(Me)_2SiO[Me_2SiO]_xSi(Me)_2CH=CH_2$ $Me_3SiO[(Me)_2SiO]_x[CH_2=CH(Me)SiO]_ySiMe_3$ wherein Me is methyl, x≧0, alternatively x is 0 to 200, alternatively x is 10 to 100, y≧2, alternatively y is 2 to 200, alternatively y is 10 to 100.

Vinyl functional polydimethylsilloxanes are known, and there are many commercially available.

In another embodiment, component (B) is selected horn a polyether compound, herein denoted as (B³), having the formula $R^2—Y^3—R^2$ compound where $R^2$ is as defined above and $Y^3$ is a polyoxyalkylene group having the formula $(C_nH_{2n}O)_b$ wherein n is from 2 to 4 inclusive, b is greater than 2, alternatively b can range from 2 to 100, or alternatively b can range 2 to 50.

The polyoxyalkylene group typically can comprise oxyethylene units ($C_2H_4O$), oxypropylene units ($C_3H_6O$), oxytetramethylene car its isomer oxybutylene units ($C_4H_8O$), or mixtures thereof. Thus, the $R^2—Y^3—R^2$ compound may be selected from a polyoxyalkylene group having the formula $R^2—O[(C_2H_4O)_f(C_3H_6O)_g(C_4H_8O)_h]—R^2$ where f, g, and h may each independently range from 0 to 1.00, providing the sum of f+g+h is greater than alternatively the sum of f+g+h ranges from 2 to 100, or alternatively the sum of f+g+h ranges from 2 to 50.

Alternatively, the polyoxyalkylene group comprises only oxypropylene units $(C_3H_6O)_g$. Representative, non-limiting examples of polyoxypropylene containing $R^2—Y^3—R^2$ compounds include;

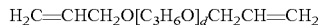

where g is as defined above.

Representative, non-limiting examples of polyoxybutylene containing $R_2—Y^3—R^2$ compounds include;

Component B) may also be a mixture of various polyethers, i.e. a mixture of B³ components.

In another embodiment, component (B) is selected from a $R^2—Y^4—R^2$ compound, herein denoted as (B⁴), where $R^2$ is as defined above and $Y^4$ is a polyalkylene group, selected from C2 to C6 alkylene units or their isomers. One example is polyisobutylene group which is a polymer containing isobutylene unit. The molecular weight of the polyisobutylene group may vary, but typically ranges from 100 to 10,000 g/mole. Representative, non-limiting examples of $R^2—Y—R^2$ compounds containing a polyisobutylene group includes those commercially available from BASF under the tradename of OPPONOL By, such as OPPONOL BY 5K, a diallyl terminated polyisobutylene having an average molecular weight of 5000 g/mole.

In yet another embodiment, component (B) is selected from a $R^2—Y^5—R^2$ compound, herein denoted as (B⁵), where $R^2$ is as defined above and $Y^5$ is a hydrocarbon-silicone copolymer group. The hydrocarbon-silicone copolymer group may have the formula

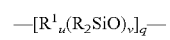

where $R^1$ and R are as defined above;

u and v are independently ≧1, alternatively u ranges from 1 to 20, alternatively v ranges from 2 to 500, or from 2 to 200, q is >1, alternatively q ranges from 2 to 500, alternatively q ranges from 2 to 100.

$R^2—Y^5—R^2$ compounds having a hydrocarbon-silicone copolymer group may be prepared via a hydrosilylation reaction between an α-ω unsaturated hydrocarbon, such as those described above as $B^1$, and an organohydrogensiloxane. A representative, non-limiting example of such a reaction is shown below.

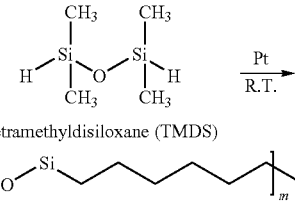
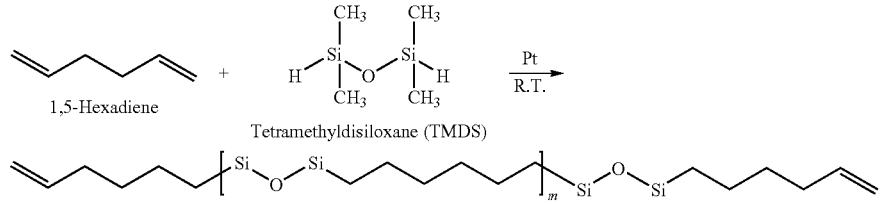

In another embodiment, component (B) is selected from poly(diene) compounds which contain vinyl or alkenyl side groups. The vinyl or alkenyl side groups are usually the reaction product of diene polymerization reaction and may be available for reaction with SiH compound. Polybutadiene is one such polymer and typically contains about 20 molar % of 1,2-vinyl side group. Ricon 130 is a commercially available liquid polybutadiene polymer with 20-35 molar % of 1,2-vinyl pendant groups, it has a viscosity of about 750 cps and molecular weight of 2500 g/mole. Ricon 130 is obtained from Sartomer Company, Inc. (Exton, Pa.).

Component (B) may also be a mixture of any diene, e or ene-yne compound, such as any combinations of $B^1$, $B^2$, $B^3$, $B^4$, and $B^5$.

The amounts of component (A) and component (B) used to prepare the present composition will depend on the individual components and the desired SiH to aliphatic unsaturation ratio. The ratio of SiH in component (A) to aliphatic unsaturation from component (B) useful to prepare the compositions of the present invention can be from 10:1 to 1:10, alternatively 5:1 to 1:5, or alternatively 4:1 to 1:4.

If components (A) and (B) are not the only materials containing aliphatic unsaturated groups and SiH-containing groups in the present composition, then the above ratios relate to the total amount of such groups present in the composition rather than only those components.

(C) The Hydrosilylation Catalyst

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willin, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lou et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as (COD)Pt(SiMeCl$_2$)$_2$, where COD is 1,5-cyclooctadiene and Me is methyl. These alkene-platinum-silyl complexes may be prepared, for example by mixing 0.015 mole (COD)PtCl$_2$ with 0.045 mole COD and 0.0612 moles HMeSiCl$_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

(D) The Carrier Fluid

The silicone elastomers may be contained in an optional carrier fluid (D). Although it is not required, typically the carrier fluid may be the same as the solvent used for conducting the hydrosilylation reaction as described above. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl {(trimethylsilyl oxy}cyclotrisiloxane well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H(C11-C12), hydrogenated polydecen. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 0 to 98 weight percent, alternatively 0.5 to 80 weight percent, alternatively 5 to 70 weight percent, of carrier fluid in composition containing (A) and (B) and (D), where the sum of (A), (B), and (D) is 100 weight percent.

E) Personal or Healthcare Active

Component E) is active selected from any personal or health care active. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter 1, of the Code of Federal Regulations, Parts 200-299 and Parts 300-499.

Useful active ingredients for use in processes according to the invention include vitamins and its derivatives, including "pro-vitamins". Vitamins useful herein include, but are not limited to, Vitamin A$_1$, retinol, C$_2$-C$_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin B$_1$, Vitamin B$_2$, Pro Vitamin B5, panthenol, Vitamin B$_6$, Vitamin B$_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucoside, sodium ascorbyl phosphate, sodium ascorbate, disodium ascorbyl sulfate, potassium (ascorbyl/tocopheryl) phosphate.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI- OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J., Component E) may also be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)]Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetrizole, Butyl Methoxydibenzoylmethane, Butyl PABA, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etocrylene Ferulic Acid, Glyceryl Octanoate Dimethoxycinnamate, Glyceryl PABA, Glycol Salicylate, Homosalate, isoamyl p-Methoxycinnamate, Isopropylbenzyl Salicylate, Isopropyl Dibenzoylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

The amount of component E) present in the silicone gel composition may vary, but typically range as follows;

0.05 to 50 wt %, alternatively 1 to 25 wt %, or alternatively 1 to 10 wt %, based on the amount by weight of silicone elastomer gel present in the composition, that is total weight of components A), B), C) and D) in the silicone gel composition.

The active, component E), may be added to the silicone gel or gel paste composition either during the making of the silicone elastomer (pre-load method), or added after the formation of the silicone elastomer gel (post load method). Alternatively, component E) may be post-added to the aqueous emulsion of the gel or gel paste.

The Silicone Elastomer

The silicone elastomers of the present invention are obtainable as hydrosilylation reaction products of components A), B), and C). The term "hydrosilylation" means the addition of an organosilicon compound containing silicon-bonded hydrogen, (such as component A) to a compound containing aliphatic unsaturation (such as component B), in the presence of a catalyst (such as component C). Hydrosilylation reactions are known in the art, and any such known methods or techniques may be used to effect the hydrosilylation reaction of components A), B), and C) to prepare the silicone elastomers of the present invention.

The hydrosilylation reaction may be conducted in the presence of a solvent, and the solvent subsequently removed by known techniques. Alternatively, the hydrosilylation may be conducted in a solvent, where the solvent is the same as the carrier fluid described as optional component D).

Gelled Compositions Containing the Silicone Elastomer

The silicone elastomers can be added to a carrier fluid (as described above as component D) to form gelled compositions, or alternatively be prepared first in a separate reaction and then added to the carrier fluid to obtain a gel. The gelled compositions of the present invention may be characterized by their hardness or firmness. Useful tests to characterize the gels are those recommended by the Gelatin Manufacturers institute of America such as the use of a "Texture Analyzer" (model TA.XT2, Stable Micro Systems, Inc., Godalming, England). The gel sample is subject to a compression test with the Texture Analyzer having a probe with a 5.0 kg load cell. The probe approaches the surface of the gel at a speed of 0.5 mm/sec and continues compression into the gel to a distance of 5.0 mm, then holds for 1 second before retreating. The Texture Analyzer detects the resistance force the probe experiences during the compression test. The force exhibited by the load cell is plotted as a function of time.

The hardness of the silicone elastomers, gels and elastomer blends (SEBs) for purposes of this invention is defined as the resistance force detected by the probe of the "Texture Analyzer" during the compression test. Two data may used to characterize hardness: Force 1, the force at the maximum compression point (i.e. the 5.0 mm compression point into the gel surface), and Area F-T: the area-force integration during the 1 second hold at the maximum compression point. The average of a total of 5 tests are typically performed for each gel.

The value obtained for Force 1 is converted into Newton (N), by dividing the gram force value by 101.97. (i.e. 1 Newton equals 101.97 g force based on the size of the probe used in this instrument). The second property reported by Texture Analyzer measurement is Area F-T1:2, in g force·sec. This is the area integration of the force vs. test time cure. This property is indicative of a gel network since it indicates ability to sustain resistance to the compression force, which is relevant to elastomers and gels. The value is reported in g force·sec, and is converted to Newton·sec in SI unit by dividing the value in g force·sec by 101.97.

The silicone gels of the present invention has a compression hardness of at least 200 Newton/m$^2$, alternatively 400 Newton/m$^2$, or alternatively 600 Newton/m$^2$.

Gel Paste Compositions Containing the Silicone Elastomer

The gelled compositions of the present invention can be used to prepare gel paste or gel blend compositions containing actives I) shearing the silicone elastomer gel, as described above,
II) combining the sheared silicone elastomer gel with additional quantities of
D) the carrier fluid, bis described above, and optionally
E) a personal or health care active
to form a gel paste or blend composition.

The silicone elastomer gel compositions of the present invention blends may be considered as discrete crosslinked silicone elastomer gel particles dispersed in carrier fluids. Thus, the silicone elastomer compositions are effective rheological thickeners for lower molecular weight silicone fluids. As such they can be used to prepare useful gel blend compositions, such as "paste" compositions.

To make such silicone elastomer blends, the aforementioned silicone elastomer gels of known initial elastomer content (IEC) are sheared to obtain small particle size and further diluted to a final elastomer content (FEC), "Shearing", as used herein refers to any shear mixing process, such as obtained from homogenizing, sonalating, or any other mixing processes known in the art as shear mixing. The shear mixing of the silicone elastomer gel composition results in a composition having reduced particle size. The subsequent composition having reduced particle size is then further combined with D) the carrier fluid. The carrier fluid may be any carrier fluid as described above, but typically is a volatile methyl siloxane, such as D5. The technique for combining the D) the carrier fluid with the silicone elastomer composition having reduced particle size is not critical, and typically involves simple stirring or mixing. The resulting compositions may be considered as a pa having a viscosity greater than 100,000 cP (mPa·s).

The silicone elastomer gel compositions can be used in a variety of personal, household, and healthcare applications. In particular, the compositions of the present invention may be used: as thickening agents, as taught in U.S. Pat. Nos. 6,051,216, 5,919,441, 5,981,680; to structure oils, as disclosed in WO 2004/060271 and WO 2004/060101; in sunscreen compositions as taught in WO 2004/060276; as structuring agents in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1,266,653, WO 03/105789, WO 2004/000247 and WO 03/106614; as structuring agents as taught in WO 2004/054523; in long wearing cosmetic compositions as taught in US Patent Application Publication 2004/0180032; in transparent or translucent care and/or make up compositions as discussed in WO 2004/054524; all of which are incorporated herein by reference.

Silicone elastomer gels can also be used in anti-perspirant and deodorant compositions under but not limited to the form of sticks, soft solid, roll on, aerosol, and pumpsprays. Some examples of antiperspirant agents and deodorant agents are Aluminum Chloride, Aluminum Zirconium Tetrachlorohydrex CA, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG. Chlorophyllin-Copper Complex, Triclosan, Aluminum Zirconium Octachlorohydrate, and Zinc Ricinoleate.

The personal care compositions of this invention may be in the form of a cream, a gel, a powder, a paste, or a freely pourable liquid. Generally, such compositions can generally be prepared at room temperature if no solid materials at room temperature are presents in the compositions, using simple propeller mixers. Brookfield counter-rotating mixers, or homogenizing mixers. No special equipment or processing conditions are typically required. Depending on the type of form made, the method of preparation will be different, but such methods are well known in the art.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for colour cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 $mg/cm^2$ to about 3 $mg/cm^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 1 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit. When a high silicone content is incorporated in a hair care composition according to the invention, this may be a useful material for split end hair products.

The compositions according to this invention can be used on the skin of humans or animals for example to moisturize, color or generally improve the appearance or to apply actives, such as sunscreens, deodorants, insect repellents etc.

The silicone resin elastomer can be used in antiperspirants, deodorants, skin creams, skin care lotions, moisturizers, facial treatments such as acne or wrinkle removers, personal and facial cleansers, sunscreens, make-ups, color cosmetics, foundations, blushes, lipsticks, lip balms, eyeliners, mascaras, and powders. Furthermore, it is anticipated that the compositions of the present invention can be combined with various other components to prepare the personal care or medical care products described infra. These components include, silicones materials, fragrances, preservatives, polyols, such as glycerin and propylene glycols, additional surfactants, moisturizers, pigments and powders, sunscreens, fragrances, emollients, structurants, thickeners, electrolytes, pH control agents, film formers, conditioning agents, botanicals (plant extracts)) and actives such as vitamins and their derivatives, antioxidants and the like, amino-acids derivatives, liposomes, antiperspirant and deodorant agents, skin bleaching agent, skin protectants, self tanning agents, and conditioning agents for hair and skin such as quaternary polymer or amino functional silicones, commonly used to formulate such personal care and medical products. This silicone resin elastomer is used in amounts of from 0.1 to 50 parts by weight, preferably from 0.5 to 20 parts by weight, most preferably from x to xx parts by weight.

The composition according to the invention may also be combined with a number of optional ingredients:

non-volatile polysiloxane having the structure:

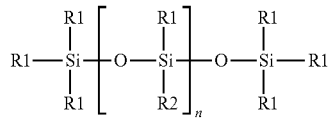

wherein has a value sufficient to provide polysiloxane polymers having a viscosity in the range of 100-10,000 min²/sec. R1 and R2 can be alkyl radicals containing 1-20 carbon atoms or aryl groups, preferably alkyl radicals containing 1-6 carbon atoms, and more preferably methyl or phenyl groups. Typically, the value of n is 20-500, more preferably 80-375. Some illustrative polysiloxane polymers include polydimethylsiloxane, polydiethylsiloxane, polymethylethylsiloxane, polymethylphenylsiloxane, and polydiphenylsiloxane.

Alkylmethylsiloxanes: These siloxane polymers generally will have the formula $Me_3SiO[Me_2SiO]_y[MeRSiO]_z SiMe_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition.

Silicone gums: Polydiorganosiloxane gums are known in the art and are available commercially. They consist of generally insoluble polydiorganosiloxanes having a viscosity in excess of 1,000,000 centistoke (mm²/s) at 25° C., preferably greater than 5,000,000 centistoke (mm²/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistokes (mm²/s) at 25° C., to about 20 million centistokes (mm²/s) at 25° C. Compositions of this type in the form of suspensions are most preferred, and are described for example in U.S. Pat. No. 6,013,682 (Jan. 11, 2000).

Silicone polyamides: Representative compositions of suitable silicone polyamide copolymers are set forth in detail in U.S. Pat. No. 5,981,680 (Nov. 9, 1999).

Silicone resins: These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Other Silicone elastomers: Such elastomers are generally reaction products obtained by combining an organopolysiloxane having an unsaturated group bound to a terminal silicon atom and an organohydrogensiloxane, and then subjecting it to at least a partial cure. One example of a suitable elastomer is a composition known in the cosmetic industry under its INCI name of Dimethicone/Vinyl Dimethicone Crosspolymer or Dimethicone Crosspolymer. Emulsions and suspension of these polysiloxane elastomers can also be used as components of the composition. Polysiloxane elastomers in the form of powders coated with different organic and inorganic materials such as mica and silica can also be used.

Carbinol Fluids: These materials are described in WO 03/101412 A2, and can be commonly described as substituted hydrocarbyl functional siloxane fluids or resins.

Water soluble or water dispersible silicone polyether compositions: These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible Compositions according to the invention can be provided in the form of water-in-oil or water-in-silicone emulsions using silicone emulsifiers. Typically, the water-in-silicone emulsifier is non-ionic and selected from the group comprising polyoxyalkylene-substituted silicones, silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al.) and include polydiorganosiloxane polyoxyalkylene copolymers containing at least one polydiorganosiloxane segment consisting essentially of $R_bSiO_{(4-b)2}$ siloxane units wherein b has a value of from 0 to 3, inclusive, there being an average value of approximately 2 R groups per silicon for all siloxane units in the copolymer, and R denotes a radical selected from the group consisting of methyl, ethyl, vinyl, phenyl, and a divalent radical bonding a polyoxyalkylene segment to the polydiorganosiloxane segment, at least 95 percent of all R being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8. Alternatively the silicone-based surfactant can be a cross-linked emulsifier in which at least two organopolysiloxane-polyoxyalkylene molecules are cross-linked by a cross-linking radical, the crosslinked organopolysiloxane-polyoxyalkylene emulsifier having the formula

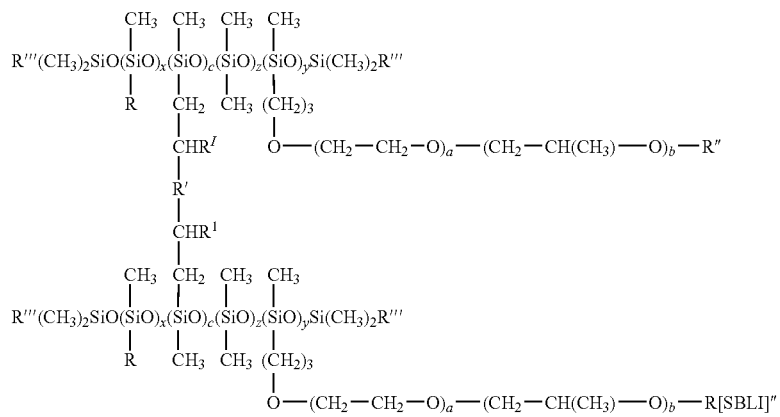

wherein the crosslinked organopolysiloxane-polyoxyalkylene emulsifier formula R is an aliphatic radical having 2 to 25 carbon atoms; R' is an organic or organosiloxane group which does not contain hydrolyzable bonds; R" is a terminal group; R''' is independently an aliphatic radical having 1 to 25 carbon atoms; $R^1$ is independently selected from the group consisting of hydrogen and an aliphatic radical containing 1-3 carbon atoms; x is an integer from 0 to 100; c is an integer from 1 to 5; z is an integer from 0 to 600; y is an integer from 1 to 10; x+y+z>40; a is an integer from 4 to 40; b is an integer from 0 to 40; a/b>1. The amount of the silicone emulsifying agent in the final composition may vary widely, but typically would be from 0.05% to 1.5%, alternatively 0.1 to 1%, more preferably 0.15 to 0.8% by weight, or alternatively 0.2 to 0.6% by weight.

The composition according to the invention can include a sunscreen as an optional or as a main ingredient. Sunscreens include hut are not limited to those components which absorb ultraviolet light between 290 and 320 nanometers, i.e., the UV-B region, such as para-aminobenzoic acid derivatives and cinnamates derivatives such as ethyl hexyl methoxy cinnamate; and those compositions which absorb ultraviolet light in the range of 320 to 400 nanometer, i.e., the UV-A region, such as benzophenone derivatives and butyl methoxy dibenzoylmethane derivatives, and hydrophilic compositions such as benzylidine-2-camphor sulphonic acid derivatives. The cosmetic compositions according to the invention can also contain pigments or alternatively nanopigments (average primary particle size: generally between 5 nm and 100 nm, preferably between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum When the composition according to the invention is an oil-in-water emulsion, it will include common ingredients generally used for preparing emulsions such as but not limited to nonionic surfactants well known in the art to prepare oil-in-water emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Compositions according to the invention can include suspending agents such xanthan gum, carboxyvinyl polymers. Examples of these polymers include Carbopol 934, 940, 941, and 956. available from B. F. Goodrich Company. Still other suitable suspending agents include di(hydrogenated tallow) phthalic acid amide, and crosslinked maleic anhydride-methyl vinyl ether copolymer, cellulose ethers derivatives, guar gum, polyvinyl alcohol, polyvinyl pyrrolidone, hydroxypropyl guar gum, starch and starch derivatives, Suitable thickening agents are exemplified by sodium alginate, gum arabic, polyoxyethylene, guar gum, hydroxypropyl guar gum, ethoxylated alcohols, such as laureth-4 or polyethylene glycol 400.

The composition according to the invention can further contain an oil or oily component. The term oil as used herein refers to any material that is substantially insoluble in water, and which is generally compatible with any low molecular weight silicone species present in the composition. When the composition is to be used in a cosmetic or personal care product, the product components must also be cosmetically acceptable, or otherwise meet the conditions of the end use of the product. Some example of suitable oil components include natural oils such as coconut oil; hydrocarbons such as mineral oil and hydrogenated polyisobutene; fatty alcohols such as octyldodecanol; esters such as C12 to C15 alkyl benzoates; diesters such as propylene dipelargonate; and triesters such as glyceryl trioctanoate. Low viscosity oils can also be used such as those oils having a viscosity of 5 to 100 mPa·s at 25° C., generally consisting of esters having a structure such as RCO—OR' wherein RCO represents a carboxylic acid radical and OR' is an alcohol residue. Some examples of low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylatelcaprate, decyl isostearate, isodecyl oleate, isodecyl neopentanoate, isohexyl neopentanoate, octyl palmitate, dioctyl malate, tridecyl octanoate, myristyl myristate, octododecanol and mixtures of octyldodecanol, Caprylic/Capric triglycerides, isododecanol, soybean oil, sunflower oil, wheat and/or cereal germ oil, sweet almond oil, jojoba oil, avocado oil, olive oil, palm oil, calophyllum, and castor oil.

Other additives can include powders and pigments especially when the composition according to the invention is intended to be used for make-up. The powder component of the invention con be generally defined as dry, particulate matter having a particle size of 0.02-50 microns. The particulate matter may be colored or non-colored (for example white). Suitable powders include but not limited to bismuth oxychloride, titanated mica, fumed silica, spherical silica beads, polymethylmethacrylate beads, boron nitride, aluminum silicate, aluminum starch octenylsuccinate, bentonite, kaolin, magnesium aluminum silicate, silica, talc, mica, titanium dioxide, kaolin, nylon, silk powder. The above mentioned powders may be surface treated to render the particles hydrophobic in nature.

The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a mixture with colored pigments, or some organic dyes, generally used as a mixture with colored pigments and commonly used in the cosmetics industry, can be added to the composition. In general, these coloring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked, copolymer microspheres such as EXPANCEL (Nobel Industrie), polytrap and silicone resin powder and microbeads (TOSPEARL from Toshiba, for example).

The waxes or wax-like materials useful in the composition generally have a melting point range of 35 to 120° C. at atmospheric pressure. Waxes in this category include synthetic wax, silicone waxes, ceresin, paraffin, ozokerite, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. Mention may be made, among the waxes capable of being used as non-silicone fatty substances, of animal waxes, such as beeswax; vegetable waxes, such as carnauba, candelilla wax; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, silsesquioxane resins, alkoxys and/or esters.

Silicone resin elastomer can also be used in anti-perspirant and deodorant compositions under hut not limited to the form of sticks, soft solid, roil on, aerosol, pumpspray. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, Zinc Ricinoleate.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics, are also well known standard methods, including washing, wiping, peeling and the like.

For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 1 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit. When a high silicone content is incorporated in a hair care composition according to the invention, this may be a useful material for split end hair products.

The compositions according to this invention can be used on the skin of humans or animals for example to moisturize, color or generally improve the appearance or to apply actives, such as sunscreens, deodorants, insect repellents, etc.

The silicone resin elastomers are particularly useful to obtain improved compatibilities with many common personal care ingredients, while maintaining sensory aesthetics.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Materials Description

The following materials were used in these examples.

Organohydrogensiloxanes $M^H T^{Pr}$ resin 1=$M^H$ propyl silsesquioxane resin (abbreviated herein as $M^H T^{Pr}$) where $T^{Pr}$ is $CH_3CH_2CH_2SiO_{3/2}$, it has a NMR derived structure of $M^H{}_{0.4651}D_{0.0177}T^{Pr}{}_{0.5172}$ and a viscosity of 25 cps. It was made from propyltrimethoxy silane following the method described in WO 2005/100444 and contained 2.38% methoxy.

$M^H T^{Pr}$ resin 2=propyl silsesquioxane resin (abbreviated herein as $M^H T^{Pr}$) where $T^{Pr}$ is $CH_3CH_2CH_2SiO_{3/2}$. It has a NMR derived structure of $M^H{}_{0.455}D_{0.017}T^{Pr}{}_{0.528}$ and Mw of 821 g/mole. It was made from propyltriethoxy silane following the method described in WO 2005/100444 and contains about 6.8% ethoxy.

$M^HQ$ resin=The particular resin used in this study has a NMR derived structure of $M_{0.413}M^H{}_{0.0090}Q_{0.497}$ and is made to about 48.6% concentration in IHD (isohexadecane). The resin solution has 0.773% [H] as measured by FTIR.

MeH CYCLICS=methylhydrogen cyclosiloxanes (MeH cyclics) having the formula $[(CH_3)HSiO]_x$ where the average value of x is 4.4.

Siloxane Polymers Containing Unsaturated Groups

VINYL SILOXANE #1=a dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 8 and having a viscosity of 4 mm²/s at 25° C.

VINYL SILOXANE #2=a dimethylhexenylsiloxy-terminated dimethylpolysiloxane of the general formula $(CH_2=CH(CH_2)_4)(CH_3)_2SiO[(CH_3)_2SiO]_{dp}Si(CH_3)_2(CH_2)_4(CH_2=CH))$, where the average degree of polymerization (dp) was 100 and a viscosity of 170 mm²/s at 25° C.

VINYL SILOXANE #3=dimethylvinylsiloxy-terminated dimethylpolysiloxane of the general formula $(CH_2=CH)(CH_3)_2SiO[(CH_3)_2SiO]_{dp}Si(CH_3)_2(CH=CH_2)$, where the average degree of polymerization (dp) was 130 and having a viscosity of 325 mm²/s at 25"C.

α,ω-unsaturated Polypropylene Oxide

PO20—Polycerin DUS-80=α,ω-bisallyl polypropylene oxide having about 20 propylene oxide (PO) units from NOF Corporation (Japan).

MPO20—Polycerin DMUS-80=α,ω-bismethallyl polypropylene oxide having about 20 propylene oxide (PO) units from NOF Corporation (Japan).

Polyunsaturated Polymers

PBD—Ricon 130 is a liquid polybutadiene polymer with 20-35 molar % of 1,2-vinyl pendant groups, it has a viscosity of about 750 cps and molecular weight of 2500 g/mole. Ricon 130 is obtained from Sartomer Company, Inc. (Exton, Pa.).

Hydrosilylation Catalyst

PT CATALYST=SLY-OFF 4000 (Dow Corning Corporation, Midland Mich.) Pt catalyst used as provided containing 0.52 weight % Pt.

Carrier Fluids

D5=decamethylcyclopentasiloxane or D5 cyclics, DC245 (Dow Corning Corporation, Midland Mich.) used as provided.

2-1184 Fluid=linear dimethylsilicone fluid of low viscosity (Dow Corning Corporation, Midland Mich.) used as provided.

IDD=isododecane obtained from Presperse, under the trade name of Permethyl 99A.

IHD=isohexadecane obtained from Presperse, under the trade name of Permethyl 101A.

IDNP=isodecyl neopentanoate obtained from ISP (International Specialty Products Co) under the trade name of CERAPHYL SLK.

TPP=triphenylphosphine

Stabilizer=Vitamin A palmitate (VAP) and butylated hydroxytoluene

Methods of Measuring Viscosity of Silicone Elastomer Blends (SEBs)

The Brookfield Helipath™ Stand, when used with a suitable Brookfield Viscometer fitted with a special T-bar type spindle, will permit viscosity/consistency measurements in relative centipoise values for materials having characteristics similar to paste, putty, cream, gelatin, or wax.

The viscosity of silicone elastomer blends was determined using a Brookfield Model RVD-II+ Viscometer with Helipath stand (Brookfield Model D) and T-Bar spindles (Brookfield Helipath Spindle Set). All were purchased from Brookfield Engineering Laboratories, Inc. (11 Commerce Boulevard Middleboro, Mass., USA).

A sample size of 100 g in a 4 oz. round jar was required. The following preparation procedure was used before measurement: the sample was de-aired first via centrifuge, then vacuum de-aired for two hours. After de-airing, the sample was conditioned for a minimum of 4 hours @25° C. The sample was positioned with T-bar spindle at center. The reading was taken according to the typical procedure for Helipath spindle.

In general, spindle 93 (T-bar spindle C) is used for the less viscous sample, spindle 95 (T-bar spindle E) for the more viscous samples. The standard setting for rpm was 2.5. The spindle speed is maintained at constant 2.5 rpm and spindle was varied to handle samples with significant viscosities.

Measurement of Silicon Elastomer Gel Hardness

The hardness or firmness) of silicone elastomer gels was characterized using a Texture analyzer (model TA.XT2, Stable Micro Systems, Inc., Godalming, England). The Gelatin Manufacturers Institute America recommends such test methods as a standard procedure.

For silicone gels and elastomer blends, a ½ inch (1.27 cm) diameter cylindrical probe made of DELRIN acetal resin (Dupont) was used for the measurement. The gel sample is subject to the compression test using the probe with the following test cycle: the probe approaches the surface of the gel at a speed of 0.5 mm/sec and continues compression into the gel to a distance of 5.0 mm, then holds for 1 second before retreating. The Texture Analyzer has a 5.0 Kg load cell to detect the resistance force the probe experiences during the compression test. The force exhibited by the load cell is plotted as a function of time.

The hardness of the silicone elastomers, gels and elastomer blends (SEBs) is defined as the resistance force detected by the probe during the compression test. Two data are used for the hardness value: Force 1: the force at the maximum compression point (i.e. the 5.0 mm compression point into the gel surface), and Area F-T: the area-force integration during the 1 second hold at the maximum compression point. A total of 5 tests were performed for each gel and the average of the five tests is reported.

Texture Analyzer used for gel hardness measurement is force in gram, as detected by the transducer. Two values are reported for gel hardness: Force 1, the force in gram registered when the probe reached its pre-programmed full indentation (or compression) in gel sample. The unit for Force 1 reading is gram force.

The value obtained for Force 1 is converted into Newton (N), by dividing the gram force value by 101.97. (i.e. 1 Newton equals 101.97 g force based on the size of the probe used in this instrument). For instance, a value of 6327 g force converts to 62.0 N.

The second property reported by Texture Analyzer measurement is Area F-T1:2, in g force·sec. This is the area integration of the force vs. test time cure. This is an indicative property of a gel network as it indicates it ability to sustain resistance to the compression force, which is relevant to elastomers and gels.

The value is reported in g force·sec, and is converted to Newton·sec in SI unit by dividing the value in g force·sec by 101.97. For instance, a value of 33,947 g force-sec is 332.9 N·s in SI units.

Example 1

Reference

Preparation of $MM^HT^{Pr}$ Silsesquioxane Resin

Siloxane resins of the general formula $MM^HT^{Pr}$ were prepared according to the procedures described in Example 2 (reference) of WO 2005/100444 A1.

The specific compositor) of $MT^H T_{Pr}$ resin 1 and $M^H T^{Pr}$ resin 2 used in this study are shown below.

|  | Example # | |
|---|---|---|
|  | 1A $M^H T^{Pr}$ resin 1 | 1B $M^H T^{Pr}$ resin 2 |
| Description | Propyltrimethoxy silane derived; made by solventless to neat materials. | Propyltriethoxy silane derived; made by solventless to neat materials. |
| Formula weight (per NMR structure), g | 85.84 | 86.23 |
| Wt % H in neat resin (in terms of [H], calculation) | 0.5418 | 0.5277 |
| Mn, (GPC) g/mole |  | 738 |
| Mw, (GPC) g/mole |  | 821 |
| Wt. % OEt or OMe | 2.38% | 6.89% |
| Wt % OH (silanol) | 0.52% | 0.94% |
| Viscosity, cps | 25.0 | 13.0 |

Example 2

Reference

Preparation of an Organohydrogensiloxane Having at Least Two SiH Containing Cyclosiloxane Rings Organohydrogensiloxanes illustrative as a part of component A) were prepared from MeH CYCLICS and VINYL SILOXANE #2. The organohydrogensiloxane intermediates were made to about 50 wt. % in D5 fluid, IDNP (isodecyl neopentanoate), and IDD (isododecane), respectively. The details of these organohydrogensiloxanes are shown in the following table

TABLE

Composition of 100 dp organohydrogensiloxane

|  | Example # | | |
|---|---|---|---|
|  | 2A | 2B | 2C |
| SiH:Vi ratio | 3.42 | 3.42 | 3.42 |
| Compound B | $M^{hex}D_{100}M^{hex}$ VINYL SILOXANE #2 | $M^{hex}D_{100}M^{hex}$ VINYL SILOXANE #2 | $M^{hex}D_{100}M^{hex}$ VINYL SILOXANE #2 |
| % Component A in mixture | 50.0 | 50.0 | 50.0 |
| Carrier fluid type | D5 fluid | Isodecyl Neopentanoate | Isododecane |
| Wt. % H, theoretical Actual amount | 0.0289 | 0.0289 | 0.0289 |
| MeH CYCLICS, g | 14.79 | 14.79 | 14.790 |
| $M^{hex}D_{100}M^{hex}$ VINYL SILOXANE #2, g | 285.23 | 285.22 | 285.36 |
| D5 fluid, g | 300.00 |  |  |
| Isodecyl Neopentanoate (IDNP), g |  | 300.04 |  |
| Isododecane (IDD), g |  |  | 300.0 |
| Sly-Off 4000 catalyst | 0.35 | 0.35 | 0.35 |
| Stabilizer (VAP/BHT @ 98.5/1.5 w/w), g | 4.0 | 3.1 | 3.10 |
| Total Batch, g | 604.37 | 603.50 | 603.61 |
| Mixture appearance | Clear, slightly yellowish mixture | Clear yellowish mixture | Clear, slightly yellow mixture |

These organohydrogensiloxanes were made by charging CYCLICS, VINYL SILOXANE #7, and the corresponding carrier fluid into a reaction flask, mixed to homogeneous. Then the mixture was catalyzed with 3-5 ppm of Pt (Sly-Off 4000 Pt catalyst solution containing 0.52 wt % Pt). The mixture was heated to 50° C. to causing an exothermic hydrosilylation reaction to occur, the temperature was then maintained between 50 and 70"C for 3 hours. Then, 0.5 to 0.75% VAP/BHT (vitamin A palmitate and butylated hydroxytoluene) stabilizer was incorporated once the reaction mixture cooled to below 40° C.

Example 3

Preparations of Siloxane Resin Polyether Gels

Anhydrous silicone polyether gels were made by reacting with a hydrophobic polyether such as α,ω-bisallyl polypropylene oxide (PO) polyether or α,ω-bis(methy)allyl polypropylene oxide (PO) polyether with SiH-functional siloxane resin in a cosmetic fluid in the presence of a Pt catalyst. The reaction product was a clear solid gel. The reaction between the siloxane resin and the diallyl PO polyethers is a quantitative, fast addition reaction. Silicone gels of desirable polyether content may be prepared by using polyether of appropriate molecular weight. To illustrate, polyethers were procured from NOF Corporation (Japan) for this study.

Silicone organic elastomer gels having different organic content by weight in the gel network are conveniently prepared. Illustrated in the following are gels having as high as about 80% hydrophobic polyether. The elastomer gel without hydrophobic polyether organic is included as reference.

|  | Example # | | | |
|---|---|---|---|---|
|  | 3A | 3B | 3C | 3D |
| Component A: SiH resin type | $M^H T^{Pr}$ resin 1 | $M^H T^{Pr}$ resin 1 | $M^H T^{Pr}$ resin 1 | $M^H T^{Pr}$ resin 1 |
| Component B: | Polycerin DMUS-80 MPO20 | Polycerin DMUS-80 MPO20 and VINL SILOXANE #3 | Polycerin DMUS-80 MPO20 and VINYL SILOXANE #3 | VINYL SILOXANE #3 |
| Wt. % Organics in gel network | 79.8 | 40.1 | 30.6 | 0.0 |
| Carrier fluid type | IHD | IHD | IHD | IHD |
| SiH:Vi ratio | 0.90 | 0.90 | 0.90 | 0.90 |
| Actual amount |  |  |  |  |
| $M^H T^{Pr}$ resin 1 | 2.747 | 1.627 | 1.358 | 0.491 |
| Polycerin DMUS-80, g | 10.855 | 5.463 | 4.176 |  |
| VINYL SILOXANE #3, g |  | 6.519 | 8.082 | 13.161 |
| IHD (Permethyl 101A), g | 66.630 | 66.471 | 66.418 | 66.469 |
| Syl-Off 4000, g | 0.04 | 0.04 | 0.04 | 0.04 |
| Total Batch, g | 80.27 | 80.12 | 80.07 | 80.16 |
| Gel appearance | Clear, colorless firm gel | Clear, colorless firm gel | Clear, colorless firm gel | Clear, colorless firm gel |
| Texture analyzer, force 1, g | 148.9 | 152.7 | 140.4 | 107.4 |
| Texture analyzer, force-time 1-2, g | 832.8 | 829.9 | 766.8 | 590.0 |
| Gel hardness (as compression strength), N/m2 | 11,525 | 11,819 | 10,867 | 8,313 |
| Viscosity of gel, N · s/m2 or poise (dyne · s/cm2) | 64,460 | 64,236 | 59,352 | 45,667 |

Example 4

Preparations of Siloxane Resin Polyether Gels

Silicone organic elastomer gels in different cosmetic fluids are conveniently prepared. Illustrated in the following are elastomer gels in Dow Corning 245 Fluid volatile silicone cyclics, Dow Corning 2-1184 Fluid (linear silicones of low viscosity), isododecane (IDD), and isodecyl neopentanoate (IDNP) organic ester solvent, all gels contain about 30% hydrophobic polyether.

|  | Example # | | | |
|---|---|---|---|---|
|  | 4A | 4B | 4C | 4D |
| Component A: SiH type | $M^H T^{Pr}$ resin 1 | $M^H T^{Pr}$ resin 1 | $M^H T^{Pr}$ resin 1 | $M^H T^{Pr}$ resin 1 |
| Component B: olefinic type | Polycerin DMUS-80 MPO20 and VINYL SILOXANE #2 | Polycerin DMUS-80 MPO20 and VINYL SILOXANE #2 | Polycerin DMUS-80 MPO20 and VINYL SILOXANE #2 | Polycerin DMUS-80 MPO20 and VINYL SILOXANE #2 |
| Wt. % Organics in gel | 30.5 | 30.5 | 30.5 | 30.5 |
| Carrier fluid type | 245 Fluid | 2-1184 Fluid | IDD | IDNP |
| SiH:Vi ratio | 0.90 | 0.90 | 0.90 | 0.90 |
| Actual amount |  |  |  |  |
| $M^H T^{Pr}$ resin 1, g | 1.412 | 1.412 | 1.414 | 1.412 |
| Polycerin DMUS-80 MPO20, g | 4.148 | 4.160 | 4.211 | 4.172 |
| VINYL SILOXNE #2, g | 8.042 | 8.053 | 8.062 | 8.062 |
| 245 Fluid, g | 66.40 |  |  |  |
| 2-1184 Fluid, g |  | 66.44 |  |  |
| IDD (Permethyl 99A), g |  |  | 66.49 |  |

-continued

| | Example # | | | |
|---|---|---|---|---|
| | 4A | 4B | 4C | 4D |
| Ceraphyl SLK (IDNP), g | | | | 66.79 |
| Syl-Off 4000, g | 0.05 | 0.05 | 0.05 | 0.05 |
| Total Batch, g | 80.06 | 80.12 | 80.23 | 80.49 |
| Gel appearance | Clear, firm gel | Clear, firm gel | Clear, firm gel | Clear, firm gel |
| Texture analyzer, force 1, g | 162.6 | 106.3 | 88.2 | 104.8 |
| Texture analyzer, force-time 1-2, g | 871.2 | 576.9 | 484.8 | 565.4 |
| Gel hardness (as compression strength), N/m2 | 12,586 | 8,228 | 6,827 | 8,112 |
| Viscosity of gel, N · s/m2 or poise (dyne · s/cm2) | 67,432 | 44,653 | 37,524 | 43,763 |

Example 5

Preparations of Siloxane Resin Polyether Gel Blends or Pastes

Silicone polyether elastomer blend in cosmetic fluids can be prepared from silicone polyether gels, according to this invention. To make silicone polyether elastomer blend, a silicone polyether gel of known initial elastomer content (IEC) is first prepared following the procedure shown above. The silicone polyether gel is then mechanically sheared or ground into small particle sizes, followed by further dilution with a cosmetic fluid to desired final elastomer content (FEC). The finished elastomer blend is an anhydrous dispersion of SPE gel particles of finite size swollen and suspended in cosmetic fluid. The SPE elastomer blend is clear and has a paste-like consistency.

Siloxane-organic elastomer blends where the organic part is a hydrophobic polyether type are prepared. They can be prepared in two steps with the step one being the formation of gels, and the step two being the reduction of gels into small particle sizes and further diluted in a solvent of choice. The final SOEB is a homogeneous blend of siloxane resin hydrocarbon gels swollen in the solvent and with a paste like consistency. Examples of the SOEBs of 40%, 30% and 0% organic content on the gel network prepared by this two step process are illustrated below.

| | Example # | | |
|---|---|---|---|
| | 5A | 5B | 5C |
| Actual composition: | | | |
| Si resin gel used | Example 3B | Example 3C | Example 3D |
| Si resin gel, g | 79.66 | 79.77 | 79.46 |

-continued

| | Example # | | |
|---|---|---|---|
| | 5A | 5B | 5C |
| Permethyl 101A (IHD), g | 25.96 | 26.22 | 37.02 |
| Total Batch, g | 105.62 | 105.99 | 116.48 |
| % FEC in SEB | 12.8% | 12.8% | 11.6% |
| SEB initial property: date taken | | | |
| SEB appearance | Clear paste | Almost clear paste | Slightly hazy paste |
| General sensory feel | Smooth, silky feel on skin | Smooth, silky feel on skin | Smooth, silky feel on skin |
| Viscosity, cps | 228,187 | 359,557 | 603,660 |

Example 6

Preparations of Siloxane Resin Polyether Gel Blends or Pastes

Siloxane-organic elastomer blends where the organic part is a hydrophobic polyether type are prepared. They can be prepared in two steps with the step one being the formation of gels, and the step two being the reduction of gels into small particle sizes and further diluted in a solvent of choice. The final SOEB is a homogeneous blend of siloxane resin hydrocarbon gels swollen in the solvent and with a paste like consistency. Examples of the SOEB prepared by this two step process are illustrated below.

| | Example # | | | |
|---|---|---|---|---|
| | 6A | 6B | 6C | 6D |
| Wt. % Organics in gel Formulation | 30.5 | 30.5 | 30.5 | 30.5 |
| Gel Example # | 4A | 4B | 4C | 4D |
| Amount Gel, g | 65.52 | 69.24 | 66.54 | 64.34 |
| 245 Fluid, g | 43.05 | | | |

-continued

| | Example # | | | |
|---|---|---|---|---|
| | 6A | 6B | 6C | 6D |
| 2-1184 Fluid, g | | 17.83 | | |
| isododecane (IDD), g | | | 31.23 | |
| Ceraphyl SLK (IDNP), g | | | | 44.19 |
| Total Batch, g | 108.86 | 87.37 | 98.05 | 108.93 |
| % FEC | 10.26 | 13.49 | 11.57 | 10.08 |
| SEB appearance | slightly hazy, colorless paste | slightly hazy, colorless paste | clear, colorless paste | clear, colorless paste |
| Average viscosity, cps | 194,519 | 275,081 | 244,732 | 175,651 |

Alternatively, siloxane-organic elastomer blends may be prepared using other processing methods and equipments such that the gellation and size reduction may occur simultaneously or sequentially to result in the same final elastomer blend. The final SOEB is a homogeneous blend of siloxane resin hydrocarbon gels swollen in the solvent and with a paste like consistency.

Example 7

Preparations of Siloxane Resin Hydrocarbon Gels

Ricon 130 was used to react with $M^H T^{Pr}$ resin 1 to form a siloxane resin and hydrocarbon network where the SiH of siloxane resin reacts with the 1,2-vinyl of PBD polymer, in the presence of a carrier fluid. The elastomer gels formed had excellent gel hardness, good clarity, and excellent processability.

Examples of siloxane resin—hydrocarbon elastomers prepared from PBD are shown below.

| | Example # | | | |
|---|---|---|---|---|
| | 7A | 7B | 7C | 7D |
| Component A: SiH type | $M^H T^{Pr}$ resin 1 | $M^H T^{Pr}$ resin 1 | $M^H T^{Pr}$ resin 1 and SiH siloxane Ex 2 | $M^H T^{Pr}$ resin 1 and SiH siloxane Ex 2 |
| Component B: olefinic type | Ricon 130 PBD | Ricon 130 PBD | Ricon 130 PBD | Ricon 130 PBD |
| Wt. % Organics in gel | 62.6 | 66.8 | 38.8 | 42.1 |
| Carrier fluid type | IDD | IDD | IDD | IDD |
| SiH:Vi ratio | 0.30 | 0.25 | 0.30 | 0.25 |
| Actual amount | | | | |
| $M^H T^{Pr}$ resin 1, g | 5.08 | 4.51 | 2.54 | 2.26 |
| SiH siloxane from Ex 2 in IDD (50% conc.), g | none | | 11.57 | 11.23 |
| Ricon 130 PBD, g | 8.52 | 9.09 | 5.28 | 5.74 |
| IDD (Permethyl 99A), g | 66.82 | 66.53 | 60.83 | 60.88 |
| Syl-Off 4000, g | 0.07 | 0.07 | 0.07 | 0.07 |
| Total Batch, g | 80.49 | 80.20 | 80.29 | 80.18 |
| Appearance of reacted mixture | Slightly hazy, hard gel | Slightly hazy, hard gel, | Clear, hard gel; cooled to slightly hazy | Clear, hard gel; cooled to slightly hazy |
| Texture analyzer, force 1, g | 561.0 | 380.2 | 199.7 | 147.4 |
| Texture analyzer, force-time 1-2, g | 2898.0 | 1984.8 | 1071.6 | 799.9 |
| Gel hardness (as compression strength), N/m2 | 43,422 | 29,428 | 15,457 | 11,409 |
| Viscosity of gel, N · s/m2 or poise (dyne · s/cm2) | 224,310 | 153,627 | 82,944 | 61,914 |

Example 8

Preparations of Siloxane Resin Hydrocarbon Gel Blends or Pastes

Siloxane-organic elastomer blends where the organic part is a hydrocarbon type are prepared. They can be prepared in two steps with the step one being the formation of gels, and the step two being the reduction of gels into small particle sizes and further diluted in a solvent of choice. The final SOEB is a homogeneous blend of siloxane resin hydrocarbon gels swollen in the solvent and with a paste like consistency. Examples of the SOEB prepared by this two step process are illustrated below.

|  | Example # | |
|---|---|---|
|  | 8A | 8B |
| Wt. % Organics in gel Formulation | 38.8 | 42.1 |
| Staring gel Example # | 7C | 7D |
| Amount gel, g | 65.34 | 64.26 |
| Isododecane, g | 24.65 | 26.00 |
| Total Batch, g | 89.99 | 90.26 |
| % FEC | 12.3 | 12.1 |
| SEB appearance | Hazy paste | Hazy paste |
| Average viscosity, cps | 220,860 | 262,647 |

Alternatively, siloxane-organic elastomer blends may be prepared using other processing methods and equipments such that the gellation and size reduction may occur simultaneously or sequentially to result in the same final elastomer blend. The final SOEB is a homogeneous blend of siloxane resin hydrocarbon gels swollen in the solvent and with a paste like consistency.

Example 9

Preparations of Siloxane Resin Polyether Gels

Other containing siloxane resins may also be used to prepared silicone organic elastomer gels and silicone organic elastomer blends subsequently. One such siloxane resin is $M^H DT_{Pr}$ resin 2. Other functionalities such as alkoxysilyl groups (e.g. methoxysilyl, ethoxysilyl) may be present in the SiH functional siloxane resins.

Silicone organic elastomer gels having different % organic content by weight in the gel network are conveniently prepared. Illustrated in the following are gels having about 40% and 30% hydrophobic polyether. The elastomer gel without hydrophobic polyether organic is included as reference.

|  | Example # | | |
|---|---|---|---|
|  | 9A | 9B | 9C |
| Component A: SiH type | $M^H T^{Pr}$ resin 2 | $M^H T^{Pr}$ resin 2 | $M^H T^{Pr}$ resin 2 |
| Component B: unsaturated olefin type | Polycerin DMUS-80 MPO20 | Polycerin DMUS-80 MPO20 and VINYL SILOXANE #3 | VINYL SILOXANE #3 |
| Wt. % Organics in gel | 40.3 | 30.5 | 0.0 |
| Carrier fluid type | IHD | IHD | IHD |
| SiH:Vi ratio | 0.90 | 0.90 | 0.90 |
| Actual amount |  |  |  |
| $M^H T^{Pr}$ resin 2 | 1.95 | 1.69 | 0.57 |
| Polycerin DMUS-80 MPO20, g | 6.24 | 4.71 |  |
| VINYL SILOXANE #3 (2-7891LV), g | 7.17 | 9.05 | 14.79 |
| IHD (Permethyl 101A), g | 75.10 | 74.67 | 74.65 |
| Syl-Off 4000, g | 0.05 | 0.07 | 0.07 |
| Total Batch, g | 90.50 | 90.19 | 90.08 |
| Gel appearance | Clear firm gel | Clear firm gel | Clear firm gel |
| Texture analyzer, force 1, g | 136.2 | 188.0 | 164.9 |
| Texture analyzer, force-time 1-2, g | 742.2 | 1015.7 | 893.3 |
| Gel hardness (as compression strength), N/m2 | 10,542 | 14,552 | 12,764 |
| Viscosity of gel, N · s/m2 or poise (dyne · s/cm2) | 57,448 | 78,617 | 69,143 |

Example 10

Preparations of Siloxane Resin Polyether Gel Blends or Pastes

Siloxane-organic elastomer blends where the organic part is a hydrophobic polyether type are prepared. They can be prepared in two steps with the step one being the formation of gels, and the step two being the reduction of gels into small particle sizes and further diluted in a solvent of choice. The final SOEB is a homogeneous blend of siloxane resin hydrocarbon gels swollen in the solvent and with a paste like consistency. Examples of the SOEBs of 40%, 30% and 0% organic content on the gel network prepared by this two step process are illustrated below,

|  | Example # | | |
| --- | --- | --- | --- |
|  | 10A | 10B | 10C |
| Actual composition: | | | |
| Si resin-PO gel Example # used | 9A | 9B | 9C |
| Gel description | $M^H T^{Pr}$ resin 2 - MPO20 gel in IHD; 40.3% organics. | $M^H T^{Pr}$ resin 2 MPO20/Si gel in IHD; 30.5% organics. | $M^H T^{Pr}$ resin 2 Si gel in IHD; 0% organics. |
| Si resin-PO gel, g | 63.68 | 64.41 | 63.87 |
| Permethyl 101A (IHD), g | 26.51 | 28.86 | 42.70 |
| Total Batch, g | 90.19 | 93.27 | 106.57 |
| SEB initial property | | | |
| SEB appearance | Clear, colorless paste | Slightly hazy paste | Hazy paste |
| General sensory feel | Thick, but turned silky smooth on skin | Thick, but turned silky smooth on skin | Very smooth, silky |
| Viscosity, cps | 160,894 | 194,911 | 322,570 |

Example 11

Preparations of Siloxane Resin Polyether Gel Blends or Pastes

Other SiH containing siloxane resins may also be used to prepared silicone organic elastomer gels and silicone organic elastomer blends subsequently. One such siloxane resin is $M^H MQ$ resin. Other functionalities such as alkoxysilyl groups (e.g. methoxysilyl, ethoxysilyl) may be present in the SiH functional siloxane resins.

Silicone organic elastomer gels having different % organic content by weight in the gel network are conveniently prepared. Illustrated in the following are gels having about 40% and 30% hydrophobic polyether. The elastomer gel without hydrophobic polyether organic is included as reference.

|  | Example # | | |
| --- | --- | --- | --- |
|  | 11A | 11B | 11C |
| Component A: SiH Type | $MM^H Q$ resin ($M_{0.413}M^H_{0.090}Q_{0.497}$; 49% conc in IHD) | $MM^H Q$ resin ($M_{0.413}M^H_{0.090}Q_{0.497}$; 49% conc in IHD) | $MM^H Q$ resin ($M_{0.413}M^H_{0.090}Q_{0.497}$; 49% conc in IHD) |
| Component B: unsaturated compound | Polycerin MDUS-80 MPO20 | Polycerin MDUS-80 MPO20 | Polycerin MDUS-80 MPO20 |
| Wt. % Organics in gel | 34.6 | 32.3 | 29.5 |
| Carrier fluid type | IHD | IHD | IHD |
| SiH:Vi ratio | 1.50 | 1.70 | 2.20 |
| Actual amount | | | |
| $MM^H Q$ resin (49% conc in IHD), g | 14.94 | 15.78 | 16.748 |
| Polycerin DMUS-80 MPO20, g | 4.70 | 4.42 | 3.626 |
| VINYL SILOXANE #2, g | 1.59 | 1.47 | 0.452 |

-continued

|  | Example # | | |
|---|---|---|---|
|  | 11A | 11B | 11C |
| IHD (Permethyl 101A), g | 58.86 | 58.39 | 51.440 |
| Syl-Off 4000, g | 0.16 | 0.16 | 0.100 |
| Total Batch, g | 80.25 | 80.22 | 72.366 |
| Gel appearance | Clear soft get | Clear soft gel | Clear, moderate firm gel |
| Texture analyzer, force 1, g | 16.9 | 34.7 | 31.4 |
| Texture analyzer, force-time 1-2, g | 100.6 | 196.0 | 177.7 |
| Gel hardness (as compression strength), N/m2 | 1,308 | 2,686 | 2,433 |
| Viscosity of gel, N · s/m2 or poise (dyne · s/cm2) | 7,787 | 15,171 | 13,754 |

Example 12

Preparation of Silicone Organic Elastomer Blends for Organic Compatibility Study Siloxane-organic elastomer blends where the organic part is a hydrophobic polyether type are prepared. They may be prepared using one direct process, as described before. Alternatively, they can be prepared in two steps with the step one being the formation of gels, and the step two being the reduction of gels into small particle sizes and further diluted in a solvent of choice. The final SOEB is a homogeneous blend of siloxane resin hydrocarbon gels swollen in the solvent and with a paste like consistency. One example of such SOEB is prepared. The gel composition and the SOEB derived from it are shown in the following two tables.

|  | Example # 12A |
|---|---|
| Component A: SiH resin type | $M^H T^{Pr}$ resin 1 |
| Component B: | Polycerin DMUS-80 MPO20 and VINYL SILOXANE #2 |
| Wt. % Organics in gel | 30.5 |
| Carrier fluid type | IHD |
| SiH:Vi ratio | 0.90 |
| Actual amount |  |
| $M^H T^{Pr}$ resin 1, g | 4.41 |
| Polycerin DMUS-80 MPO20, g | 12.97 |
| VINYL SILOXANE #2, g | 25.13 |
| IHD (Permethyl 101A), g | 207.54 |
| Syl-Off 4000, g | 0.12 |
| Total Batch, g | 250.18 |
| Gel appearance | slightly yellow firm gel |
| Texture analyzer, force 1, g | 75.7 |
| Texture analyzer, force-time 1-2, g | 418.3 |
| Gel hardness (as compression strength), N/m2 | 5,859 |
| Viscosity of gel, N · s/m2 or poise (dyne · s/cm2) | 32,377 |

|  | Example # 12B |
|---|---|
| SOEB description | Siloxane resin and MPO20 SOEB in IHD @ 13.4% FEC. 30% Organics |

-continued

|  | Example # 12B |
|---|---|
| Actual composition: |  |
| Si resin-MPO gel used | Example 12A |
| Gel description | $M^H T^{Pr}$ resin 1 and MPO20/Si gel in IHD; 30.6% organics. |
| Si resin-MPO gel, g | 160.94 |
| Permethyl 101A (IHD), g | 42.24 |
| Total Batch, g | 203.18 |
| % FEC in SEB | 13.5% |
| SEB initial property |  |
| SEB appearance | Clear paste |
| General sensory feel | Initially slightly heavy, turned silky, smooth on skin |
| Viscosity, cps | 389,328 |

Example 13

Comparative

Compatibility of the Siloxane Organic Elastomer Blends

To demonstrate the improved compatibility of the SOEB of this invention with common personal care ingredients. The SOEB is mixed with the selected personal care ingredient at a 75/25 wt ratio (except vitamin A palmitate). The mixtures are evaluated and ranked according to the keys in the footnote of the following table. A commercial silicone elastomer blend (SEB) from Dow Corning was used as reference. The results are shown below.

| Silicone Elastomer Type | | Gel made in Example 12B | Dow Corning 9040 SEB |
|---|---|---|---|
| SEB/SOEB description |  | $M^H T^{Pr}$ resin 1 and MPO20 SOEB at 13.4% FEC in IHD; 30% organics. | 12.5% FEC in 245 Fluid; 3% organics |
| % Organics in elastomer gel network |  | 30 | 3 |
| SEB appearance |  | Clear paste | Clear paste |
| Ethylhexyl Methoxycinnamate (OMC), 25% | Sunscreen UVB | H-1-1 | H-2-5 |

-continued

| Silicone Elastomer Type | | Gel made in Example 12B | Dow Corning 9040 SEB |
|---|---|---|---|
| Octyl salicylate, 25% | Sunscreen UVB | H-1-1 | H-2-4 |
| Vitamin A Palmitate, 10% | vitamin | H-1-1 | H-1-4 |
| EtOH, 200 proof, 25% | Solvent | H-1-1 | N-3-4 |
| C12-C15 Alkyl benzoate, 25% | Emollient, ester | H-1-1 | H-3-4 |
| PPG-15 Stearyl ether, 25% | alkoxylated alcohol | H-2-2 | H-3-4 |
| Caprylic/Capric triglyceride, 25% | fats & oils | H-1-1 | H-3-4 |
| Squalane, 25% | hydrocarbons | H-3-3 | H-3-3 |
| Petrolatum, 25% | hydrocarbons Clear | H-3-5 | H-3-5 |

RATING Keys:
First key: Mixture appearance? H = Homogeneous; N = Not Homogeneous
Second key: mixture viscosity: 1 = Paste; 2 = Viscous; 3 = Liquid.
Third key: Clarity: 1 = Clear. 2 = Almost clear. 3 = Hazy. 4 = Hazy/cloudy. 5 = Cloudy Significantly better compatibility with personal care ingredients are shown for the SOEB, as compared to the conventional SEB in all three keys: the mixture of SOEB with selected personal care ingredients (EtOH ethanol, C12-C15 alkyl benzoate, Caprylic/carpric triglyceride). Most of the SOEB/ingredient mixture are much more viscous than the 9040 SEB/ingredient counterpart, another indication of better compatibility and thickening benefit. And lastly, better clarity was found in many of the SOEB/ingredient mixtures.

The invention claimed is:
1. A gel composition comprising:
a silicone elastomer from the reaction of;
A) an SiH containing organopolysiloxane silsesquioxane resin comprising the formula;

where a is greater than 0, c is from 0 to 0.4, d is from 0 to .9, with the provisos that sum of a, c, and d, is at least 0.9 and d is greater than 0,
R' is a monovalent hydrocarbon group having 2 to 8 carbon atoms, and Me is methyl,
B) an organic compound having at least two aliphatic unsaturated groups and in its molecule of the formula $H_2C=CHCH_2[C_3H_6O]_gCH_2CH=CH_2$, or $H_2C=C(CH_3)CH_2[C_3H_6O]_gCH_2C(CH_3)=CH_2$ where g is eater than 2, and
C) a hydrosilylation catalyst, and;
D) carrier fluid selected from decamethylcyclopentasiloxane, isododecane, isohexyldecane, or isodecyl neopentanoate,
E) an optional personal or healthcare active, wherein the gel composition has a hardness of at least 0.03 Newton force.
2. The composition of claim 1 wherein the molar ratio of A)/B) is from 10/1 to 1/10.
3. The composition of claim 1 wherein E) is a personal care active selected from a vitamin, sunscreen, plant extract, or fragrance.
4. The composition of claim 1 wherein E) is a health care active selected from a topical drug active, protein, enzyme, antifugual, or antimicrobial agent.
5. A personal care composition selected from a color cosmetic, a lipstick, a foundation, a shampoo, a hair conditioner, a hair fixative, a shower gel, a skin moisturizer, a skin conditioner, a body conditioner, a sun protection product, an antiperspirant, and a deodorant, wherein the personal care composition contains the composition of claim 1.

* * * * *